United States Patent [19]

Čermák et al.

[11] Patent Number: 4,962,036
[45] Date of Patent: Oct. 9, 1990

[54] MICROORGANISM DETERMINATION WITH A SORBENT PACKED COLUMN

[75] Inventors: Pavel Čermák; Václay Monhart; Jiře,acu/i Horák; Marie Tlustáková; Miroslav Paroubek, all of Prague, Czechoslovakia

[73] Assignee: Ceskoslovenska akademie ved, Prague, Czechoslovakia

[21] Appl. No.: 101,376

[22] Filed: Sep. 25, 1987

[30] Foreign Application Priority Data

Sep. 29, 1986 [CS] Czechoslovakia ............... 6957-86

[51] Int. Cl.$^5$ .................. C12Q 1/04; C12Q 1/02; C12N 11/08; C12M 1/00
[52] U.S. Cl. ........................ 435/34; 435/29; 435/30; 435/36; 435/38; 435/174; 435/177; 435/180; 435/261; 435/287; 435/288; 435/291; 435/803
[58] Field of Search ............ 435/13, 29, 30, 34, 435/174, 176, 177, 180, 261, 288, 287, 291, 803, 36, 38

[56] References Cited

U.S. PATENT DOCUMENTS

| | | | |
|---|---|---|---|
| 3,402,103 | 9/1968 | Amberg et al. | 435/161 X |
| 4,286,061 | 8/1981 | Messing et al. | 435/176 |
| 4,332,694 | 6/1982 | Kalal et al. | 435/180 X |
| 4,634,604 | 1/1987 | Tlustakova et al. | 428/407 X |

Primary Examiner—David M. Naff
Attorney, Agent, or Firm—Leydig, Voit & Mayer

[57] ABSTRACT

Determination of microorganisms in body fluids for diagnosis is carried out by passing a body fluid through a column packed with a sorbent which traps microorganisms contained by the body fluid. A culture medium is added to the column, and after culturing the presence of microorganisms is determined. The column is a substantially cylindrical body and is connected via a porous partition to a conical terminal at each end. One conical terminal is an inlet and the other is an outlet. A sorbent porous material is positioned between the partitions and the partitions have different porosities. Total inner volume of the column is about 30 to 300 ml, and volume ratio of the cylindrical body to the conic terminals is about 1:0.3 to 1:5. Preferably, the volume of the cylindrical body is about 10 to 100 ml and the total volume of the both conic terminals is about 20 to 200 ml.

8 Claims, 1 Drawing Sheet

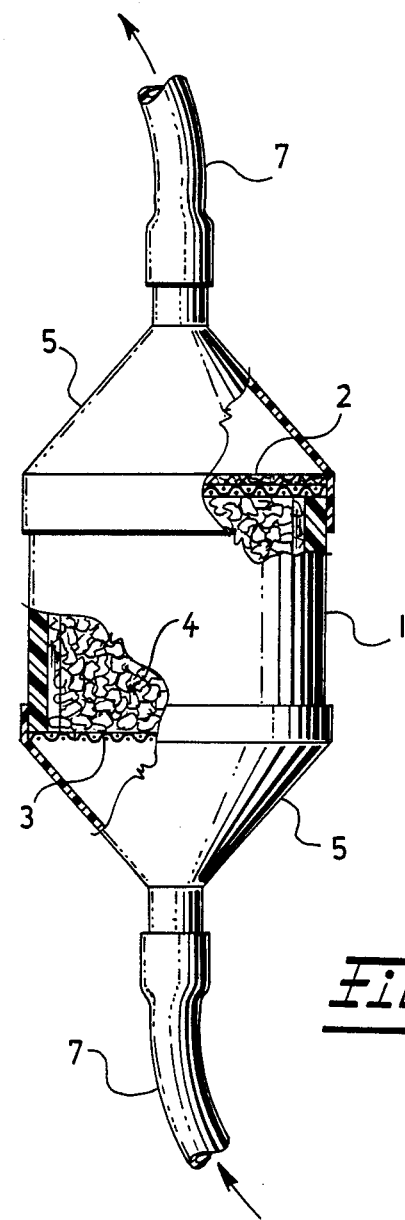
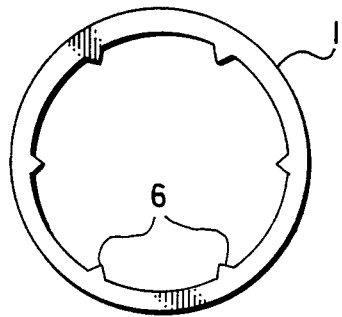
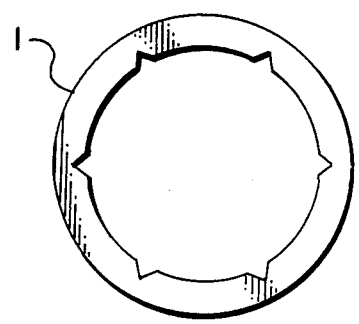

MICROORGANISM DETERMINATION WITH A SORBENT PACKED COLUMN

The invention pertains to a method for the determination of the presence of microorganisms in body liquors and to a diagnosis column for performing this method.

Numerous serious pyrexiae in medicine are caused by microbial infection where the etiologic agent occurs in circulating blood of patient in various amounts and for various periods of time. The usual method of its detection by single or repeated sampling into a vessel with culture medium does not render satisfactory results.

An efficient method for the detection of a microbial agent of pyrexial infection in blood is diagnostic perfusion. Blood of the examined person flows through a column packed with sorbent particles for a chosen period of time. The entire blood volume of blood of an adult patient passes through the column in 60 minutes at the flow rate of 100 ml.min$^{-1}$.

Only one type of diagnosis column is used currently in the world (Keller, F.; Feldman, K.; Abshagen, U. et al.: Klin. Wochenschr., 59, 1981, no. 9, p. 425–429; Matthali, D.; Kramer, P.) Grieben, K. et al.: Contr. Nephrol., 32, 1982, p. 175–180). This column is packed with surface-modified, activated charcoal. Its body is formed by a short and broad cylinder with both ends provided with external threads. Very flat terminals are screwed on the threads which accommodate seal mouldings acting as screens. For the purpose of activation, this type of column has to be opened by unscrewing the terminal and removing the screen. Then the grains of surface-modified charcoal can be transferred into a culture medium.

A method for the determination of the presence of microorganisms causing septic states in body liquors according to the present invention avoids the disadvantages connected with dismantling the column and transferring the sorbent into a culture medium outside the column. Body liquor is first allowed to flow through a column that is packed with a sorbent which traps microorganisms. The residual body liquor is forced out from the column by means of physiological saline, after which the column is filled with a culture medium in such a way that the all sorbent is immersed, and cultivation is carried out directly in the column. Upon completion of the cultivation, the culture medium is discharged from the column by suction, and the presence of microorganisms is determined by known methods.

A diagnosis column for performing the method according to the invention is made from a biocompatible material, has smooth inner surface provided, advantageously, with longitudinal ribs, is packed with a sorbent placed between partitions made from a porous material, and is characterized by a jacket consisting of a cylindrical body 1 and conical terminals 5 with a mutual volume ratio of 1:0.3 to 1:5 and the supporting partitions having different porosity.

Another feature of the diagnosis column for performing the method according to the invention consists of its total inner volume of 30 to 300 ml. The volume of the column cylindric body 1 is about 10 to 100 ml and the total volume of both terminals 5 is roughly 20 to 200 ml. The partitions separating the sorbent may have different porosity, whereas the partition near the outlet terminal is advantageously formed from several layers with different porosity, namely 2000 to 80, 150 to 50, and 80 to 20 micrometers. The inner surface of column body may be advantageously provided with ribs.

The diagnosis column according to the invention is packed with a sorbent advantageously coated with a protective layer of bicompatible polymer of a methacrylate or acrylate type in the amount of 0.01 to 20 weight %.

The diagnosis column according to the invention is diagrammatically shown in the following drawings, where FIG. 1 shows a longitudinal cross-sectional view of the column, and FIGS. 2 and 3 show a horizontal cross-section through the column provided with ribs.

FIG. 1 shows a simplified, cross-sectional view of the column according to the invention. The column consists of a column body 1 which is connected, via porous partitions 2 and 3 separating the sorbent 4, which concial terminals 5 which have attached inlet and outlet tubes 7. The arrow S in FIG. 1 indicates the direction of blood flow. An arbitrary number of ribs 6 may be provided.

FIG. 2 and 3 diagrammatically show the horizontal cross-sections with marked ribs. An arbitrary number of ribs 6 may be provided.

The material for the column has to be strong, biocompatible, nonthrombogenic, and capable of withstanding sterilization. Polypropylene, ethylene-propylene copolymers, polycarbonates, poly(tetrafluoroethylene) and similar materials can be used. These polymers may be processed by injection moulding or extrusion blowing. The shape of the column is a suitable compromise between the demands on blood when flowing through the column, and technical and economical aspects of production. The column must have a smooth inner surface advantageously provided with longitudinal ribs 6, which assist in directing the blood flow, reducing the motion of sorbent grains 4, and increasing the strength of the jacket. The column body 1 and the conic terminals 5 are designed in such a way that the transitions between them are completely smooth. Each connection between body 1 and terminal 5 may be realized by adhesion, or by heat, ultrafrequency or ultrasound welding.

The interior space contained by terminals 5 and column body 1 are separated by screens 2,3, which act as the support of sorbent 4 inside the column, on one hand and prevent penetration of the sorbent into the terminals 5 or even as far as into the blood circulation of patient at the same time. The screens 2,3 may be made from stainless steel, synthetic fabric, or plastic moulding. Their material has to meet the same conditions as the material chosen for the column jacket. A polypropylene or polyester fabric or porous polyurethane may be used. Both screens 2,3 may have the same or different density. It is advantageous to use a denser screen 2 in the outlet terminal where it acts as a protection against the penetration of thrombs, which may be form in the column, into the blood circulation of the patient. However, such columns can be used only in one direction and the blood-flow direction has to be indicated on the jacket. The mesh size of screen 2 may range from 40 micrometers to the an upper limit which is given by the grain size of the sorbent 4. The screens 2,3 may be multiple and consist of several layers of different porosity.

The sorbent 4 is packed into the column by an isotonic apyrogenic solution of sodium chloride before the outlet terminal with screen 2 is attached. The sorbent 4 may be active charcoal (preferably made from coconut shells) or a synthetic resin. The optimum size of particles is 0.3 to 0.7 mm.

The packed column is then closed with the upper terminal, provided with tubes 7 at both ends and sterilized for 2 hours at 120° C. in an autoclave.

Once charged with sorbent 4, sealed, and sterilized, the column is ready for use. After passing the patient's blood through it, microbial cells with be trapped on the surfaces of sorbent 4. Their detection and closer determination require cultivation of the sorbent in a culture medium suitable for the growth of microbes. The diagnosis column according to the invention is designed in such a way that cultivation can be carried out directly inside the column in a liquid culture medium. Opening of the column and handling of the sorbent are omitted along with possible contamination of the column content and laboratory personnel.

The tubes 7 at both ends of the column may serve as conduits for the liquid content of column (i.e., discharging of the liquid content, charging with a culture medium, inoculation of the grown microbial culture), because they can be easily punctured with a hypodermic needle and the fluid content may be handled by means of a syringe. An air filter trapping the contingent air contamination can be set on the end of tube 7 during discharging the fluid content of column.

All types of liquid culture media, either commercial or prepared in laboratory, may be used as the cultivation charge. The volume of culture medium must be sufficient to immerse all particles of the sorbent 4.

Microorganisms are trapped above all in a biological coating which is formed on the surface of the sorbent particles, through which blood flows inside the column. Blood coagulation has an important roll in the formation of this coating. A fibrin network is formed on the surface of the particles which traps blood platelets, a small number of red and white blood cells, and other corpuscles including microorganisms. Besides simple adherence of microorganisms to the surface of particles, above all a mechanical trappiung of microorganisms in the fibrin network and various specific and nonspecific receptors and ligands contribute to this process.

The sorbent particles 4 may be made from an inorganic or organic substance, from their combination, or from laminated materials. They may have various shapes, sizes and internal structures. Application of a biocompatible material is suitable as it prevents formation and growth of thrombs on particles.

The diagnostic column according to the invention has many advantages in comparision with similar columns used in world. A firm connection of the column body 1 with terminals 5 allows the necessary column sterility of much better than does the commonly used screw closure with any uncertain tightness. This substantially extends the expiration time, i.e., the period of time in which, the column may be used which is advantageous from the point of view of production, as well as of clinical practice. The column, according to the invention, is designed in such a way that it enables the cultivation of trapped bacteria without opening and handling of the sorbent. It is suited for the work in a closed and strictly sterile system which excludes the possibility of contamination from the environment and depreciation of the results of investigation. At the same time, the risk of infection of the medical and laboratory personnel is reduced to minimum. It enables optimum conditions for trapping and cultivation of bacteria from blood and thus substantially improves the diagnostics of septic states.

The invention is further described in the following examples of performance, without limiting its scope to these examles by any means.

EXAMPLE 1

The diagnosis column with volume 50 ml made from polypropylene (screens with the mesh size 290 micrometers) and packed with active charcoal derived from coconut shells (Chemviron SC XII) with an untreated surface was used in the experiment with an animal infected with rod-like bacteria Escherichia coli.

Haemoperfusion was carried out for 1 hour at the rate 20 ml/min. Upon conclusion of haemoperfusion, the tube was punctured at the end of column and the liquid content was removed by suction with a hypodermic syringe and needle. The column was then charged in the same way with a culture medium (liver stock) in an amount such that the sorbent was completely immersed. The column charged with the culture medium was allowed to sit for 24 hours at 37° C. After completing the activation, a sample of culture medium was withdrawn in the same manner as used earlier to discharge the column. The propagated bacteria were proved microscopically and by further cultivation on solid cultivation substrates.

EXAMPLE 2

The diagnosis column with volume 30 ml made from polypropylene (screens with the mesh size 300 micrometers) and packed with active charcoal having the, whose surface has been modified with 3 wt. % of poly(2-hydroxyethyl methacrylate) was used in the experiment with an animal infected with rod-like bacteria Escherichia coli. Haemoperfusion was carried out for 1 hour at the rate 20 ml/min. After 24 hours of cultivation, bacteria was isolated from a culture medium in the column.

EXAMPLE 3

The diagnosis column with volume 70 ml made from polypropylene (screens with the mesh size 300 micrometers) and packed with active charcoal derived from coconut shells (Chemviron SC II), whose surface had been modified with 3 wt.% of poly(2-hydroxyethyl methacrylate) was used in the experiment with an animal infected with coccobacillus Staphylococcus aureus. Haemoperfusion was carried out for 1 hour at the rate 20 ml/min. After 24 hours of cultivation, the bacteria was isolated from a culture medium in the column.

EXAMPLE 4

The diagnosis column with volume 50 ml made from polypropylene (screens with the mesh size 290 micrometers) and packed with active charcoal (Chemviron SC XII) with untreated particle surfaces was used in the experiment with an animal infected with coccobacillus Staphylococcus aureus. Haemoperfusion was carried out for 1 hour at the rate 20 ml/min. The bacteria was isolated from a culture medium in the column after 24 hours of cultivation.

EXAMPLE 5

The diagnosis column with volume 150 ml from poly(tetraethylene) (screens with the mesh sizes—inlet screen 200 micrometers, outlet screen 75 micrometers) and packed with a styrene-divinylbenzene copolymer (Synachrom E5) was used in the experiment with an animal infected with rod-like bacteria Escherichius coli. Haemoperfusion was carried out for 1.5 hours at the rate 20 ml/min. The bacteria was isolated from a culture medium in the column after 24 hours of cultivation.

EXAMPLE 6

The diagnosis column with volume 100 ml made from poly(tetrafluoroethylene) (screens with mesh sizes—inlet screen 290 micrometers, outlet screen 150 micrometers and packed with a styrene-divinylbenzene copolymer (Persorb) was used in the experiment with an animal infected with rod-like bacteria Escherichia coli. Haemoperfusion was carried out for 1 hour at the rate 25 ml/min. Bacteria were isolated from a culture medium in the column after 24 hours of cultivation.

EXAMPLE 7

The diagnosis column with volume 300 ml made from polypropylene (screens with the mesh size 214 micrometers) and packed with the styrene-divinylbenzene copolymer (Persorb) whose surface had been modified with 0.1 wt. % of poly(2-hydroxypropyl acrylate) was used in the experiment with an animal infected with coccobacillus Staphylococcus aureus. Haemoperfusion was carried out for 2 hours at the rate 18 ml/min. Bacteria were isolated from a culture medium in the column after 24 hours of cultivation.

We claim:

1. A method for determining the presence of a microorganism in a body liquor, comprising: (1) allowing the body liquor to flow through a column packed with a sorbent to trap the microorganism; (2) activating the trapped microorganism in a culture medium, by forcing the body liquor out from the column by means of physiological saline, charging the column with a culture medium, and, after cultivation is completed, removing the culture medium from the column by suction; and (3) determining the presence of the microorganism in the medium; wherein the column comprises a substantially cylindrical column body connected at each end via porous partitions having different porosities to conical terminals, one of said conical terminals having an inlet for the column and the other of said conical terminals having an outlet, all components of the column being made from biocompatible material and having a smooth inner surface, the column having a sorbent placed between said partitions, said partitions supporting said sorbent and being made from a porous material, the total inner volume of the column being from about 30 to about 300 ml, and the volume of the body of the cylindrical column being about 10 to 100 ml and the total volume of both conic terminals of the column being about 20 to 200 ml.

2. The method of claim 1 wherein the ratio of volume of the substantially cylindrical body of the column to the volume of the conic terminals of the column is about 1:5.

3. A diagnostic column for determining the presence of a microorganism in a body liquor, comprising a substantially cylindrical column body connected at each end via porous partitions having different porosities to conical terminals, one of said conical terminals having an inlet for the column and the other of said conical terminals having an outlet, all components of the column being made from biocompatible material and having a smooth inner surface, the column having a sorbent capable of trapping said microorganism placed between said partitions, said partitions supporting said sorbent and being made from a porous material, the total inner volume of the column being from about 30 to about 300 ml, and the volume of the body of the cylindrical column being about 10 to 100 ml and the total volume of both conic terminals of the column being about 20 to 200 ml.

4. The diagnostic column according to claim 3, wherein the substantially cylindrical column has internal longitudinal ribs.

5. The diagnostic column according to claim 1, wherein the partition at said outlet terminal has a lower porosity than that of the partition at the inlet terminal.

6. The diagnostic column according to claim 5, wherein the partition at the outlet terminal is formed from three layers with different porosites and wherein the porosities of the individual layers of the partition are 2000 to 80 $\mu$m, 150 to 50 $\mu$m, and 80 to 20 $\mu$m, respectively.

7. The diagnostic column according to claim 3 wherein the sorbent packed in said column is coated with a protective layer of a biocompatible material.

8. The diagnostic column according to claim 7, wherein said biocompatible material is an acrylate or methacrylate, and is present in an amount from 0.01 to 20 weight %, based upon the weight of said sorbent.

* * * * *